United States Patent [19]

Kusmierczyk et al.

[11] Patent Number: 5,368,559
[45] Date of Patent: Nov. 29, 1994

[54] METHOD AND APPARATUS FOR INCREASING THE PRESSURE IN A MEDICAL PUMPING SYSTEM

[75] Inventors: Robert C. Kusmierczyk, Pinellas Park; Brian D. Dross, Gulfport; Fred B. Dinger, III, Belleair, all of Fla.

[73] Assignee: Linvatec Corporation, Largo, Fla.

[21] Appl. No.: 959,239

[22] Filed: Oct. 9, 1992

[51] Int. Cl.⁵ .............................................. A61M 1/00
[52] U.S. Cl. .......................................... 604/28; 604/31
[58] Field of Search ................... 604/30, 31, 66, 67, 604/28, 49; 417/300, 309

[56] References Cited

U.S. PATENT DOCUMENTS

| | | | |
|---|---|---|---|
| 3,261,541 | 7/1966 | Kocher | 417/309 |
| 4,555,645 | 11/1985 | Atkinson . | |
| 4,561,431 | 12/1985 | Atkinson . | |
| 4,586,920 | 5/1986 | Peabody | 604/31 |
| 4,626,239 | 12/1986 | Ardizzone | 604/31 |
| 4,635,621 | 1/1987 | Atkinson . | |
| 4,679,596 | 7/1987 | Olson . | |
| 4,902,277 | 2/1990 | Mathies et al. | 604/67 |

*Primary Examiner*—Jerome L. Kruter
*Attorney, Agent, or Firm*—Rosenblatt & Associates

[57] ABSTRACT

A simple and inexpensive method and apparatus are provided for increasing the pressure at which fluid may be delivered by a lavage/irrigation system.

9 Claims, 1 Drawing Sheet

METHOD AND APPARATUS FOR INCREASING THE PRESSURE IN A MEDICAL PUMPING SYSTEM

FIELD OF THE INVENTION

The present invention provides a method and apparatus by which a relatively low pressure medical lavage-/irrigation system can be converted to perform procedures, such as hydrodissection or other medical procedures, which typically require relatively high pressures.

BACKGROUND OF THE INVENTION

The term "lavage" has been used in the literature in a somewhat ambiguous manner. Sometimes, the term is used to refer to the washing of tissue using a pulsating stream of fluid. The term also is used to describe aspiration of tissue. As used herein, the term "lavage" is used in its broadest sense, and is intended to refer to any one of, or combinations of, irrigation, pulsatile lavage, and aspiration of tissue. As used herein, lavage can be accomplished with a stream of fluid at a relatively low pressure.

A number of systems for performing lavage are available, most of which are mechanized. Some of the available systems theoretically may be used to perform medical procedures which require a fluid stream delivered at higher pressures; however, the pressure setting mechanism of most of the available lavage systems cannot be set beyond approximately 0–150 mm Hg. Much higher pressures, e.g., 0–1500 mm Hg, are required to perform high pressure procedures such as hydrodissection.

Of course, one could design a lavage system in which the pump could be set to deliver fluid at higher pressures; however, many already have purchased lavage systems which cannot be set at such high pressures. Therefore, an inexpensive but effective means for adapting relatively low pressure lavage systems so that they can produce high pressure fluid streams for medical procedures would be desirable.

SUMMARY OF THE INVENTION

The present invention provides a simple, inexpensive means for converting existing, relatively low pressure lavage systems into systems capable of producing high pressure fluid streams which may be used, e.g., for hydrodissection. According to the present invention, the pumping system of a typical lavage system is provided with an additional line (a "pressure decrease line") which connects the fluid supply line and the pressure sensing line. The pressure decrease line drains fluid from the pressure sensing line so that the pressure sensed in the pressure sensing line is less than the actual pressure in the demand line. The larger the diameter of the pressure decrease line, the lower the sensed pressure. The resulting measured decrease in the sensed pressure makes the existing control system push the pump to provide greater output pressure. The fluid stream delivered by such a system may be enhanced, e.g., to 25 or more times than the set pressure in the controller.

DETAILED DESCRIPTION OF THE INVENTION

Figure 1:
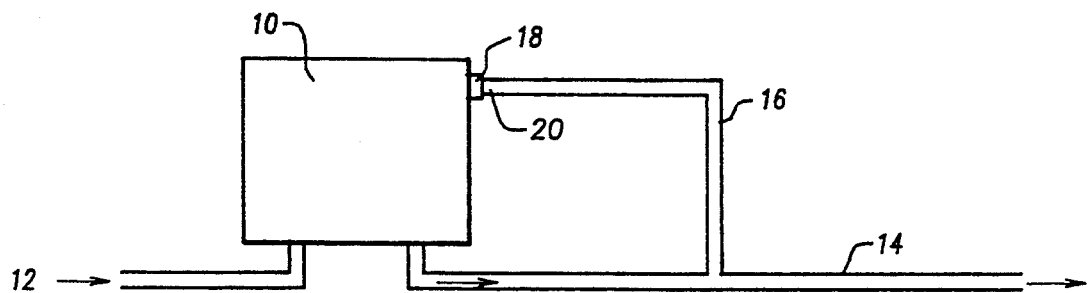
FIG. 1 is a diagrammatic representation of a typical lavage system which cannot be used according to the present invention.

Referring to FIG. 1, a typical lavage system includes a pump 10, a supply line 12, a demand line 14, and a pressure sensing line 16. The pressure that is generated by pump 10 is set using known means. Information about the pressure in the demand line 14 is monitored and fed back to the pump 10 by a pressure sensor or pressure transducer 18, which typically is located at the pump end 20 of pressure sensing line 16. The information from the pressure sensor 18 typically is used to control the output of the pump 10 so that the desired output pressure corresponds to the set pressure.

In most applications, the sensed pressure and the desired output pressure will be the same. However, some applications may require an output pressure that is higher than the highest pressure at which the lavage system can be set. In these high pressure applications, it may be necessary for the output pressure to exceed the sensed pressure.

Figure 2:
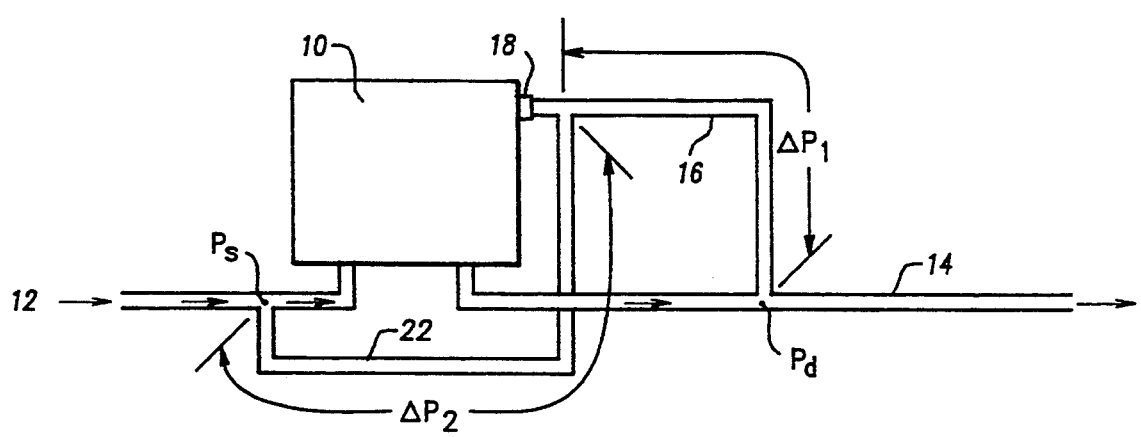
FIG. 2 is a diagrammatic representation of the lavage system of FIG. 1 after being adapted for use according to the present invention.

FIG. 2 is a diagrammatic representation of a lavage system according to the present invention in which the output pressure can exceed the sensed pressure. The system diagrammed in FIG. 2 essentially is the same as the system diagrammed in FIG. 1 except for the addition of a pressure decrease line 22. The pressure decrease line 22 extends between the supply line 12 and the pressure sensing line 16.

The pressure decrease line 22 may be added to substantially any lavage system; however, the preferred embodiment disclosed herein includes a linear motor. The amount of pressure generated by a linear motor varies with the stroke length and/or speed of the motor; therefore, a linear motor can generate higher pressures by increasing the pump stroke length and/or speed without any substantial change to the motor. A preferred lavage system for use in the present invention is the system described in U.S. Pat. No. 4,561,431, incorporated herein by reference. The lavage system may be modified to include the pressure decrease line 22 of the present invention using any suitable means, e.g., "T"-adapters. The desired increase in the pressure of the fluid delivered can be achieved by using a pressure decrease line 22 having a particular diameter. The greater the diameter of the pressure decrease line 22, the greater the decrease in sensed pressure and the greater the increase in pump output to try to reach the set point of the controller.

The present invention now will be described in operation. In the following description, $\Delta P_1$ is the pressure drop across the pressure sensing line 16 and $\Delta P_2$ is the pressure drop across the pressure decrease line 22. Fluid enters the pump 10 at a first pressure ($P_s$=supply side line pressure) and exits the pump at a second pressure ($P_d$=desired output pressure). The pressure sensor 18 attempts to measure $P_d$; however, the pressure decrease line 22 drains fluid from the pressure sensing line 16 causing a drop in the sensed pressure, $P_{sensed}$. The following mathematically describes the resulting sensed pressure:

$$P_{sensed} = \frac{P_s \Delta P_1 + P_d \Delta P_2}{\Delta P_1 + \Delta P_2}$$

The pump continues to increase its output pressure in order to cause $P_{sensed}$ to approach the set pressure. As a result, the desired output pressure $P_d$ will be substantially higher than the set pressure:

$$P_d = \frac{P_{sensed}[\Delta P_1 + \Delta P_2] - P_s \Delta P_1}{\Delta P_2}$$

The invention is useful in lavage systems that may be already in possession by a user. The user may desire an economical way to convert an existing system to deliver more flow and/or pressure. If the controller has a low preset range, the invention allows use of the same controller but at a different range. Thus higher pressure applications are possible without significant modifications to the controller. Full use of the available pump output becomes an economic reality without expensive component replacement.

One of skill in the art will appreciate that many modifications may be made to the embodiment described herein and explained in the accompanying figures without departing from the spirit of the invention. Accordingly, the embodiment described herein is illustrative only and is not intended to limit the scope of the present invention.

We claim:

1. A control system modification for modifying the controlled pressure range of an existing control device used in performing medical procedures comprising a pumping system with a pump, discharge and suction lines connected to said pump, and a first pressure sensing line connected between a pressure sensing means and said discharge line, said pressure sensing means connected to a control device to regulate discharge line pressure, said control device capable of pressure regulation to a predetermined value or values within a predetermined range, said modification comprising:
    a second pressure sensing line in pressure communication on one end with said first pressure sensing line;
    a pressure source at a different pressure than said discharge line;
    said second pressure sensing line having one end connected to said different pressure source, said controller sensing said different pressure than the actual discharge line pressure and in response altering the output of the pump and modifying the pressure range within which said control system can operate.

2. The apparatus of claim 1 wherein said pressure source is a suction line on a pump.

3. A control system modification for a pumping system for medical procedures comprising:
    a pump;
    a suction line;
    a discharge line;
    a control system to sense the discharge line pressure and to regulate it at any setpoint within a predetermined range of the control system; and
    means for modifying the control system by altering the sensed pressure to allow operation of the same control system at a different control range than said predetermined range.

4. The control system modification of claim 3, further comprising a pressure sensing line between said discharge line and said control system wherein:
    said means for modifying the control system further comprises:
    a line in fluid communication with said sensing line adapted to lower the sensed pressure of the control system without materially altering the discharge line pressure thereby allowing the control system to operate in a different range than said predetermined range.

5. The control system of claim 4 wherein:
    said line is also in fluid communication with said suction line.

6. The control system of claim 5 wherein:
    said control system regulates the output of said pump to regulate discharge line pressure.

7. A method for varying the range of pressure within which a fluid system for medical procedures operates, said method comprising the steps of:
    providing a fluid system adapted to treat mammalian tissue, said fluid system having a pump, a suction, a discharge line, and an existing controller for sensing pump output pressure of the discharge line at a sensed pressure point, and for regulating said discharge line pressure at a setpoint within a preset range;
    providing a flow conduit connected near said sensed pressure point;
    connecting said flow conduit to a source of pressure that differs from said discharge line pressure;
    using said flow conduit to alter the pressure sensed by said controller to a pressure that differs from said actual discharge line pressure, thereby causing said fluid system to operate within a pressure range that differs from said setpoint within said preset range.

8. The method of claim 7 further comprising the steps of:
    connecting the flow conduit to the suction line.

9. The method of claim 7 further comprising:
    connecting the flow conduit to a sump from which the pump draws through the suction line.

* * * * *